United States Patent [19]
Shpuntov et al.

[11] Patent Number: 5,917,928
[45] Date of Patent: Jun. 29, 1999

[54] SYSTEM AND METHOD FOR AUTOMATICALLY VERIFYING IDENTITY OF A SUBJECT

[75] Inventors: Mikhail Shpuntov, Brooklyn, N.Y.; Alexandre Pletnev, Moscow, Russian Federation; Mikhail Berestetskiy, Brooklyn, N.Y.

[73] Assignee: BES Systems, Inc., Brooklyn, N.Y.

[21] Appl. No.: 08/891,958

[22] Filed: Jul. 14, 1997

[51] Int. Cl.$^6$ .................................................. G06K 9/00
[52] U.S. Cl. .......................................... 382/124; 382/209
[58] Field of Search ..................................... 382/124, 125, 382/209, 216, 217, 218; 356/71

[56] References Cited

U.S. PATENT DOCUMENTS

| | | | |
|---|---|---|---|
| 3,716,301 | 2/1973 | Caulfield et al. | 356/71 |
| 4,581,760 | 4/1986 | Schiller et al. | 382/124 |
| 4,641,350 | 2/1987 | Bunn | 382/124 |
| 5,040,223 | 8/1991 | Kamiya et al. | 382/124 |
| 5,067,162 | 11/1991 | Driscoll, Jr. et al. | 382/125 |
| 5,261,008 | 11/1993 | Yamamoto | 382/124 |
| 5,537,484 | 7/1996 | Kobayashi | 382/124 |
| 5,633,947 | 5/1997 | Sibbald | 382/124 |

*Primary Examiner*—Joseph Mancuso
*Attorney, Agent, or Firm*—Cohen, Pontani, Lieberman & Pavane

[57] ABSTRACT

A system and method for verifying identity of a user seeking access to a secured area or object is provided. The system employs a novel global image comparison approach by first acquiring a reference fingerprint image from a user during an enrollment stage, obtaining a set of multiple reference segments from the reference image representative of unique portions thereof, and later during a verification stage obtaining a verification fingerprint image from a user seeking access to the secured area or object, determining the most likely positions for the multiple reference segments over the verify image, and then comparing all pixels of the reference image enclosed by the multiple reference segments to all pixels in a portion of the verify image overlaid by the multiple reference segments in their current positions over the verify image in accordance with a dynamically determined threshold that is individually tailored for the user providing the reference image during the enrollment stage. When the threshold is exceeded, the user seeking access is granted access to the secured object or area; otherwise the user is rejected. The system of the present invention includes the capability of determining multiple most likely positions for the multiple reference segments over the verify image and then sequentially matching the reference segments to the verify image portion overlaid by them in their current position against the dynamic threshold until a match is found or until it is determined that the verify and reference images are not matched. To speed up the verification process, the verify image and one of the multiple reference segments may be temporarily coarsened during the process of determining multiple possible most likely positions for the multiple reference segments.

17 Claims, 9 Drawing Sheets

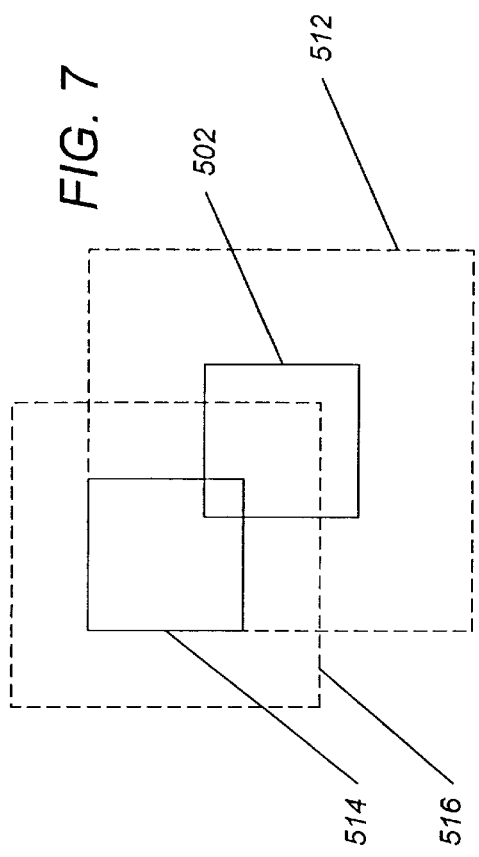
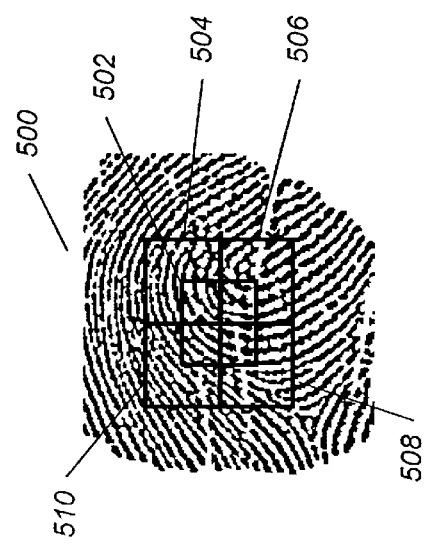
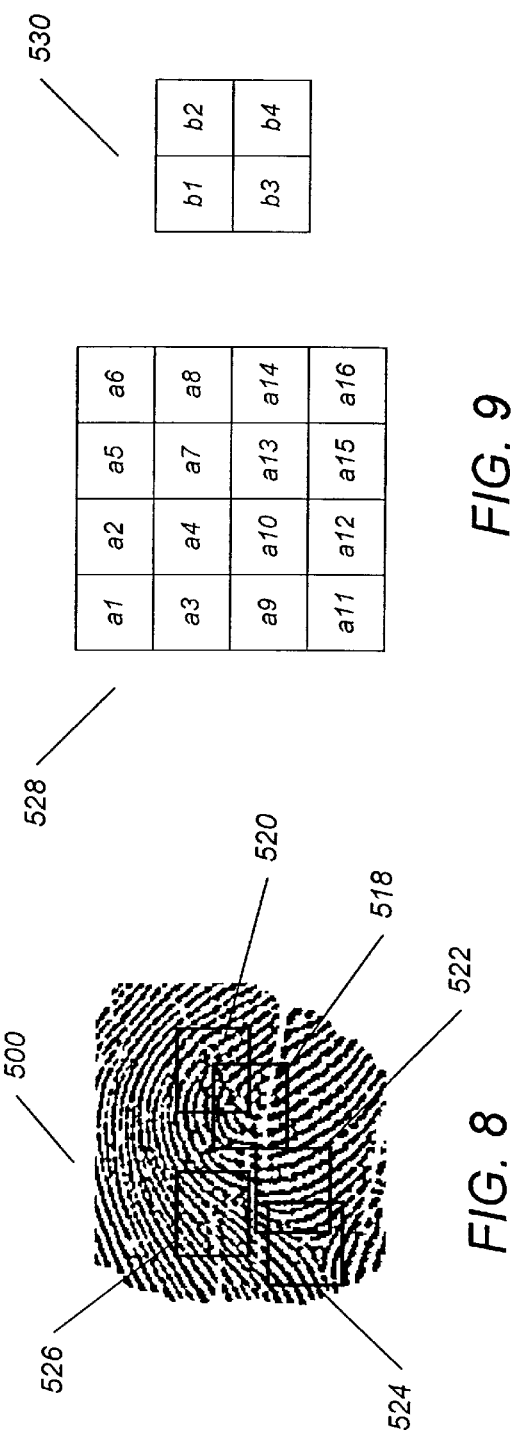
FIG. 7
FIG. 9
FIG. 6
FIG. 8

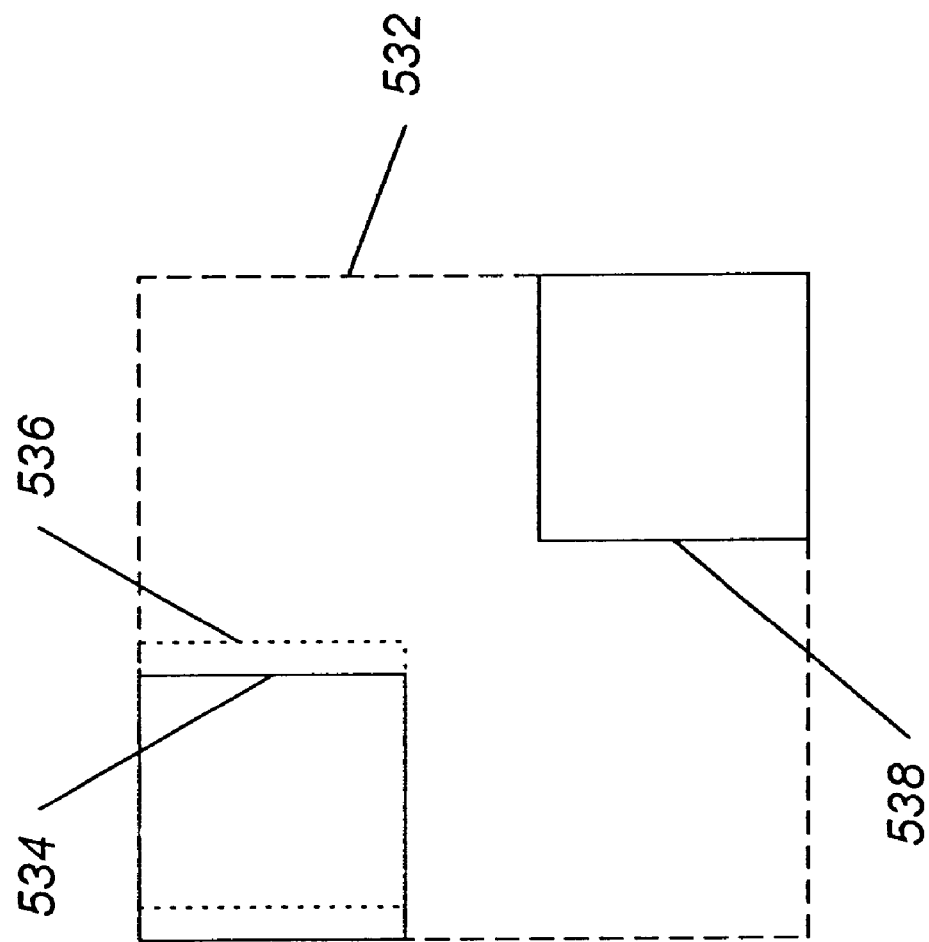

SYSTEM AND METHOD FOR AUTOMATICALLY VERIFYING IDENTITY OF A SUBJECT

FIELD OF THE INVENTION

The present invention relates generally to automatic identity verification systems, and more particularly to an identity verification system for automatically verifying the identity of a subject using a fingerprint image.

BACKGROUND OF THE INVENTION

Identity verification using fingerprint images is a science that has developed steadily over many years. Traditionally, matching fingerprint images was a painstaking process of manually comparing a set of subject's fingerprint images ("search" prints) to a multitude of "file" fingerprint image sets. A typical file fingerprint set comprised a group of inked fingerprints, such as those made by law enforcement agencies after an arrest, or made during the process of application to certain civil service positions. A fingerprint expert with a magnifying device would spend hours pouring over hundreds of file fingerprint images in an attempt to match a search fingerprint image to an existing file image.

It could be easily appreciated that the manual fingerprint matching process was extremely time-consuming and error-prone. Furthermore, poorly obtained or incomplete search and file fingerprint images often made the process even more difficult. In order to address these problems, a number of manual fingerprint image matching techniques were developed. The most popular technique involved identifying certain distinctive characteristics, or minutiae, present in every fingerprint image. Common minutiae include such fingerprint characteristics as bifurcations and ridge endings. Minutiae were typically recorded with three coordinates: two coordinates "x" and "y" representative of the minutia's position relative to a coordinate system, and an angle "v" representing the average direction of lines in the vicinity of the minutia. Combinations of minutiae and their locations are unique to each individual. Thus, for easier future verification and classification, fingerprint images were represented by sets of minutiae and their coordinates. While this development improved the accuracy and speed of verification, manually matching minutiae was still a slow and arduous task.

Another, less popular fingerprint classification technique involved classifying fingerprints by pattern types. The various pattern types included arches, tented arches, loops and whorls. The patterns were matched by their number, relative location and orientation.

Soon after the computer revolution of the 1960's, numerous attempts to automate the fingerprint verification process were made. The approach of matching entire fingerprint images was quickly discarded as being too computation intensive. Instead, the technique of classifying fingerprint images by their minutiae was computerized, greatly improving the speed and accuracy over that of the manual process. For many years thereafter, developments in computer processing power and refinements to the minutiae identification algorithms further improved the speed and accuracy of the process.

Advancements in automated fingerprint minutiae identification made feasible the use of automatic fingerprint image verification systems for verifying identity of a subject in real time. Thus, a new security process of restricting access to secure areas to authorized personnel using fingerprint images was introduced. This was accomplished by enrolling authorized personnel into a fingerprint record database stored in a computer system by scanning in a selected fingerprint image of an authorized person and locating and recording coordinates of that fingerprint's minutiae in a minutia record stored in the computer system's memory. Typically, a fingerprint scanner was connected to an electronic locking mechanism of a door, such that a person desiring access to the area beyond had to place a designated finger on the scanning device so that a search fingerprint image could be obtained. The search fingerprint image was then compared to the multitude of file fingerprint images to determine whether the person was authorized to enter the area.

To speed up the identification process, in later systems authorized persons were given additional identifying elements, such as personal identification numbers (PINs) or magnetic strip cards embedded with identifying data. These elements were associated with the authorized person's minutia record. Typically these improved systems would work as follows: A person desiring access to an area first inputs an identifying element into an identification system, for example by entering a PIN code on a keypad, or by swiping a magnetic strip card. Then, the person places a designated finger on a scanning device so that a search fingerprint image is entered into the system. The system then retrieves the file fingerprint image associated with the identifying elements provided by the person and attempts to verify the person's identity by comparing the search and file fingerprint images with each other. If the minutiae coordinates and angles on the file and search images match, the person is allowed entry into the secured area; otherwise, entry is denied.

This approach is problematic for a number of reasons. Minutia are notoriously difficult to identify in a large number of cases. Furthermore, if even a small amount of minutia is missing from a search fingerprint image, perhaps due to dirt or a scratch on the fingerprint portion of the finger, the system would not provide positive identification. Even relatively slight angular motion of a person's finger during the process of scanning of the search fingerprint image may generate errors. Moreover, because minutiae are numerous and because several coordinates need to be stored for each minutia, a minutiae record consumes a significant amount of data storage space on a computer system in which it is stored.

Most importantly, the task of identifying and locating minutiae in a search fingerprint image and then matching the minutiae to a minutiae record of a file fingerprint image is extremely computation intensive and thus requires very significant computer processing power and resources. In an installation with multiple secure areas, even a high speed computer system would suffer a increasing slowdown if a number of identification processes were taking place simultaneously. Typically, even with powerful computer systems, the wait for identification can be as long as several seconds, and much longer in a large installation with many fingerprint identification security entry points. To compound the frustration of waiting for a positive identification, a person may be asked to repeat the procedure several times, if, for example, the person moved their finger during the acquisition of the search image.

A recent attempt to address the above problems was disclosed in U.S. Pat. No. 5,067,162 to Driscoll, Jr. et al. (hereinafter "Driscoll"). Driscoll teaches that instead of identifying minutiae on a fingerprint image, a plurality of small "reference sections" of a fingerprint, each containing a portion of the fingerprint image data, and their coordinate positions should be identified and stored in a reference record after the image is binarized (i.e., converted into a black and white digital format). Verification is performed by first scanning a search fingerprint image of a person claiming to be authorized, forming a verification image with a plurality of verify regions each corresponding to a position of one of the reference sections, determining a best match location, corresponding to a reference section at each verify region and then determining whether a match exists by determining the degree of similarity between: (1) image data of each best match location and the corresponding reference section, and (2) the relative positioning of the best match locations and the corresponding reference sections.

While the Driscoll approach solves some of the problems inherent in traditional minutiae identification, improving the accuracy and removing the requirement that the search fingerprint image be nearly perfect, it has a significant drawback. While the Driscoll system is less error prone than a typical minutia verification system, if a portion of a person's fingerprint which encompasses one or more reference sections is obscured by dirt or damaged by a scrape or the like, the verification accuracy drops significantly resulting in authorized persons being denied access because Driscoll requires that a substantial number of the individual reference sections are matched to particular verify regions on the search fingerprint image and because Driscoll relies on the relative positioning of the reference sections for match determination.

It would thus be desirable to provide a system and method for automatically verifying the identity of a subject using a fingerprint image with a high degree of speed and accuracy. It would further be desirable to ensure a high degree of accuracy even if the subject's fingerprint image to be verified is only partially visible due to damage or contamination.

SUMMARY OF THE INVENTION

The disadvantages and limitations discussed above are overcome by the present invention. The present invention provides a system and method for verifying identity of a user seeking access to a secured area or object. The system of the present invention operates in two separate stages—an enrollment stage and a verification stage. The system of the present invention includes a control unit for executing an enrollment control program during the enrollment stage and executing a verification control program during the verification stage, a memory for storing data and the control programs, an image scanner for acquiring reference and verify images, and optional input and output devices.

During the enrollment stage, a reference fingerprint image of a person to be enrolled as an authorized user of the system is obtained. The reference image is then filtered and binarized. The control unit then selects a predefined number of candidate reference segments, where each segment is selected from within a predefined area of the reference image by sequentially testing each possible location for each reference segment for uniqueness, and saving the image data of the most uniquely positioned reference segments, one of such segments being designated as primary and the others as secondary. The locations of the secondary reference segments relative to the primary reference segment are also stored. Finally, a dynamic threshold is obtained by the control unit as a function of uniqueness of each of the reference segments.

During the verification stage, a verify fingerprint image of a person claiming to be an authorized user of the system is obtained. The verify image is then optionally filtered and binarized. The control unit then retrieves the reference image data of the enrolled person, matching the primary reference segment against a predefined area of the verify image to determine at least one best match position, matching the secondary reference segments against respectively defined search areas in the verify image, whose locations are determined by the at least one best-match position of the primary segment, and verifying the identity of the person claiming to be enrolled by calculating a first summary pixel value of all reference segments at their respective best-match positions, a second summary pixel value of all pixels of the verify image overlaid by the reference segments at their best match positions, and comparing the summary pixel values to each other in accordance with the dynamic threshold. If more than one best match position was found for the primary reference segment, the secondary reference segments are repositioned in accordance with the next best match position and the comparing process is repeated. To speed up the determination of the best match positions, the verify image and the primary reference segments may be temporarily coarsened by a predetermined factor.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawings, wherein like reference characters denote elements throughout the several views:

FIGS. 6 to 10 are diagrams representative of exemplary results of functions performed during the operation of the system of FIG. 1 in accordance with the present invention.

DETAILED DESCRIPTION OF PREFERRED EMBODIMENTS

Although the present invention is described with reference to identifying, comparing, and verifying fingerprint images, it should be understood that the system and methods of present invention may be applied to other forms of image recognition and image comparison applications, such as in medical imaging systems.

Figure 1:
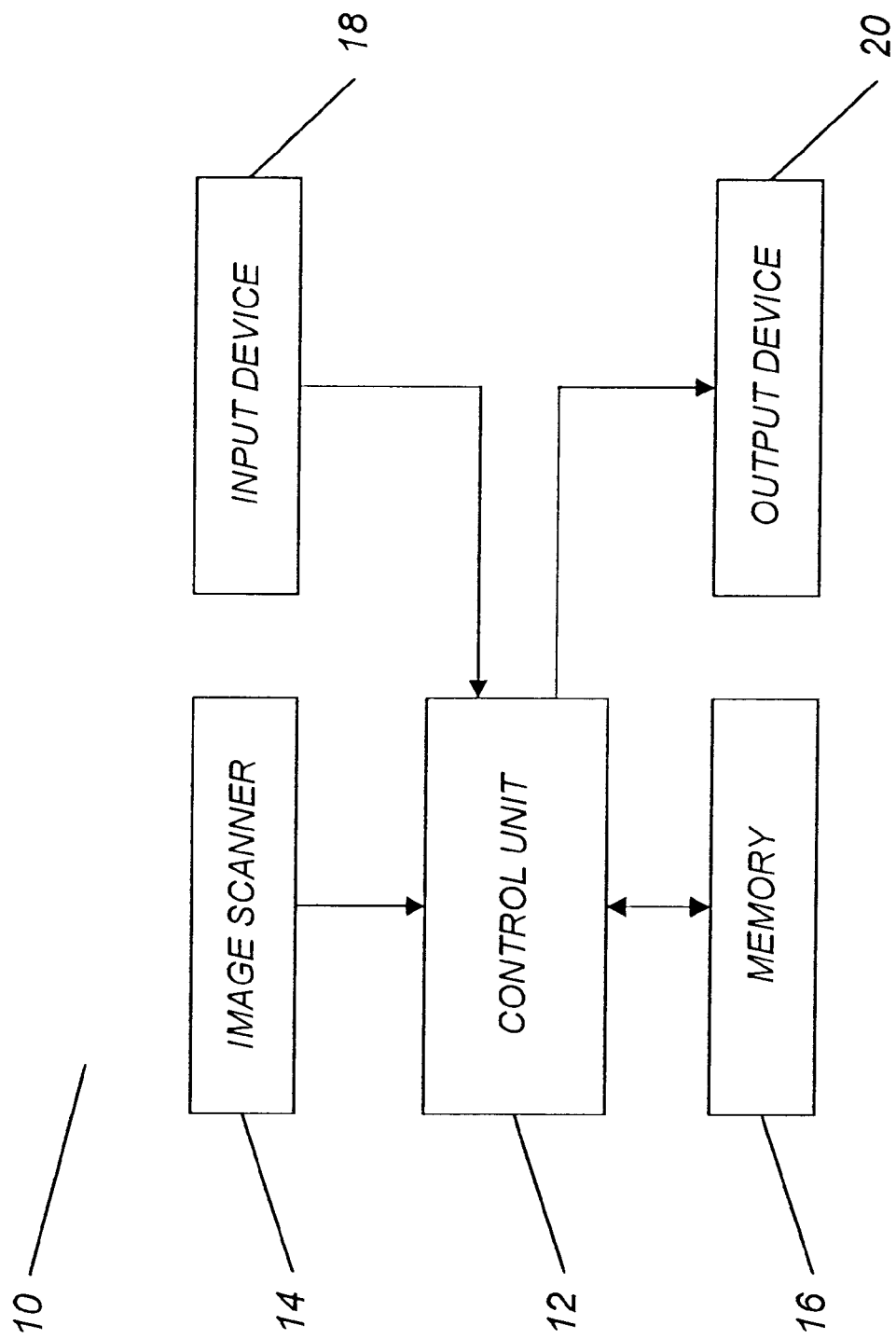
FIG. 1 is a schematic block diagram of a system for automatically verifying the identity of a subject using a fingerprint image.

Referring initially to FIG. 1, an identity verification system 10 for securing access to an area or an object is shown. For example, the identity verification system 10 may be connected to a door actuation mechanism to restrict access through the door to users authorized to use the identity verification system 10. In another example, the identity verification system 10 may be used to restrict access to an object, such as a computer terminal, by allowing only users authorized to use the identity verification system 10 to access the computer terminal.

In summary, the identity verification system 10 operates in two separate stages. During a first enrollment stage a user is enrolled in the identity verification system 10 by providing a fingerprint image and additional identifying data for permanent storage in the identity verification system 10.

Later, at a second verification stage, a user seeking access to an area or object secured by the identity verification system 10 provides a fingerprint image and the additional identifying data for comparison with the additional identifying data and the fingerprint image already stored in the identity verification system 10. If the newly provided additional identifying data matches the additional identifying data stored in the identity verification system 10 and if the newly provided fingerprint image substantially matches the fingerprint image stored in the identity verification system 10 as determined by a verification threshold computed by the identity verification system 10 or provided by an operator, the user is granted access to the secured area or object. Otherwise, the identity verification system 10 rejects the user's access request.

The operation of the identity verification system 10 is controlled by a control unit 12, which preferably contains control circuitry and a microprocessor (not shown) for executing control program instructions that are stored in a memory 16. The memory 16 preferably includes a long term storage memory (not shown) for storing data and control programs and a short term program memory (not shown) for temporarily storing control program instructions and variables during the execution of the control program by the control unit 12. The control unit 12 and the memory 16 may be implemented together in a personal or portable computer or in a proprietary unit. The control unit 12 may be connected to an actuating device (not shown) such as a lock or an on/off switch that may be selectively activated by the control unit 12. An image scanner 14 for acquiring a fingerprint image from a user is connected to the control unit 12. The image scanner 14 may be any scanner suitable for obtaining fingerprint images, such as an optical or a charge coupled device scanner. An optional input device 18 may be connected to the control unit 12 for acquiring additional identifying data from the user supplying a fingerprint for scanning by the image scanner 14; the additional data being associated, by the control unit 12, with the fingerprint image acquired by the image scanner 14 and subsequently stored in the memory 16. The input device 18 is preferably a keyboard or a keypad, but may be any device for acquiring alphanumeric data such as a speech recognition system or a magnetic card reader. In addition, the input device 18 may include an image capture device for acquiring an image of the user.

An optional output device 20 may be connected to the control unit 12 for displaying the acquired fingerprint image and additional identifying data to the user and/or an operator of the identity verification system 10. The output device may also be used for monitoring, by the operator of the identity verification system 10, of the execution of the control program instructions by the control unit 12. The output device is preferably a video display monitor that may comprise a standard CRT or an LCD panel.

Before describing the present invention in greater detail, it is helpful to describe a technique known in the image processing art for determining the degree of similarity between two identically sized images. Each image typically consists of a number of uniform pixel zones. For example, a 1-bit black and white image consists of two uniform zones—the black pixel zone and the white pixel zone. Each uniform zone typically has a different amount of pixels. In accordance with the present invention, when two images are compared, a response function (hereinafter "RF") value indicative of the degree of similarity between the first image and the second image is obtained by comparing corresponding uniform zones of each image. A high RF value is indicative of a high degree of similarity between the images, while a low RF is indicative of a low degree of similarity. Preferably, the RF value is normalized such that the minimum RF is 0, indicating that the images being compared are completely different (such as comparing a completely black image to a completely white image), while a maximum RF is 1, indicating that the images being compared are identical (such as comparing a completely black image to another completely black image). The RF may also be used to determine a particular image's uniqueness by comparing the particular image to a number of other images, where when the RF values of the comparison operations are uniformly low, the particular image has a relatively high degree of uniqueness. The normalized value of the RF may be computed by one of a number of techniques known in the image processing art.

Figure 2:
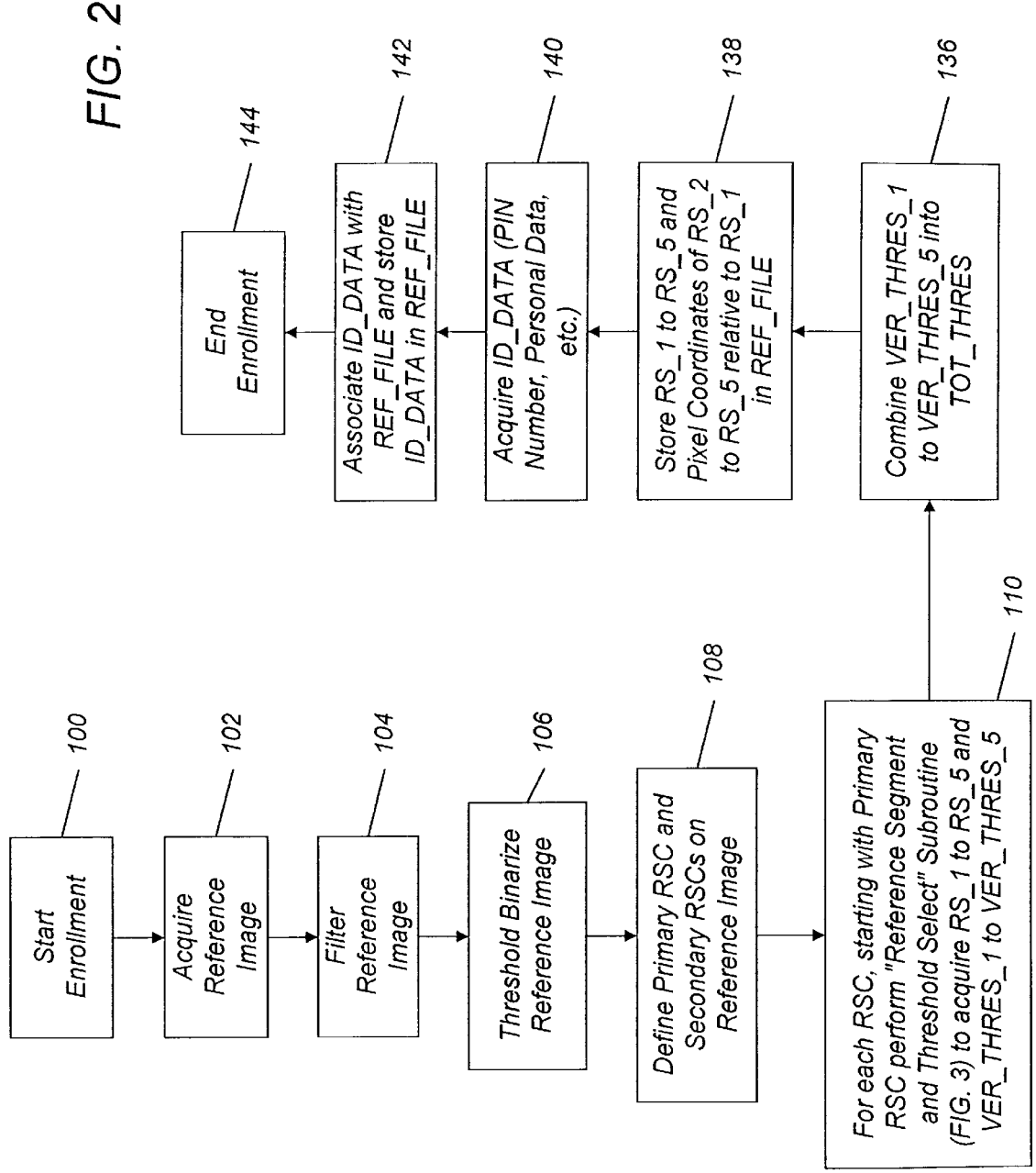
FIGS. 2 to 5B are logic flow diagrams representative of the functional operation of the system of FIG. 1 in accordance with the present invention.

Referring now to FIG. 2, a logic flow diagram representing an enrollment control program for the control unit 12 of FIG. 1 in accordance with a preferred embodiment of the present invention is shown. After the operator begins the program at step 100 and instructs the user to be enrolled to place a predetermined finger on the image scanner 14, the control unit 12 acquires a fingerprint reference image (hereinafter "reference image") from the image scanner 14 at step 102. Typically, the reference image is obtained in halftone form commonly having 256 gray levels.

At an optional step 104, the reference image may be filtered, for example using a moving window filter, selected from those well known in the image processing art, in order to suppress random noise. Other image processing filter operations may also be performed on the reference image at this step. At step 106, the reference image is preferably binarized. The initial stage of binarization involves removing large scale brightness variations in the reference image in accordance with a dynamically determined threshold. The dynamic threshold may be constructed in a window of a predefined size that is moved by the control unit 12 across the entire reference image. For each location of the window, a cumulative distribution function (hereinafter "CDF") of all pixel values of the reference image that are within the window is calculated, and the median of the CDF is determined. The CDF may be determined in a number of ways well known in the art. The value of the CDF median is used as the dynamic binarization threshold for a current central pixel of the window. This process is repeated for all possible locations of the moving window on the original image. Preferably, a current central pixel of the moving window is recalculated by an expression:

$$z' = z\frac{M_0}{M'}$$

where z is the original value (i.e., brightness) of the central pixel, z' is its new value, M is the CDF median for the current location of the moving window, and $M_0$ is a predefined constant value selected as a matter of design choice. Thus, in effect, the new reference image produced by this processing will have the same CDF median at all locations. This processing removes any large-scale brightness variations in the image.

At a second binarization stage, the reference image is subjected to coarse quantization in order to reduce the amount of bits representing each pixel. A typical number of bits per pixel in a scanned reference image is 8, allowing for 256 different gray levels. An image having a high amount of bits per pixel imposes proportionally greater storage and processing requirements on an image processing system.

Thus, in cases where the halftone level of an image is not important, such as in fingerprint images, it is desirable to reduce the number of bits per pixel in an image in order to reduce storage and processing requirements. The bit-per-pixel reduction is relatively easy to accomplish. For example, to reduce an 8-bit reference image to a 4-bit, or a 16 gray level image, then every 16 consecutive gray levels in the original reference image are merged into a single gray level in the new reference image. Specifically, gray levels 0 to 15 are merged into new gray level 0, gray levels 16 to 31 are merged into new gray level 1, and so forth, with gray levels 240 to 255 merged into new gray level 15. Preferably, during the second binarization stage the reference image is reduced from an 8-bit image to a 1-bit image, merging gray levels 0 to 127 into a new gray level 0, and merging gray levels 128 to 255 into a new gray level 1. To binarize the reference image with the least possible loss of information, $M_0$ in the initial binarization stage is preferably set to 128.

At step 108, the control unit defines a predetermined number of reference segment candidates (hereinafter "RSCs") positioned and overlaid over the reference image. Referring now to FIG. 6, five RSCs 502–510 are shown overlaying an exemplary binarized reference image 500. The particular number, size, and initial positions of defined RSCs are a matter of design choice; the five RSCs 502–510 and their initial positions shown in FIG. 6 were selected purely by way of example.

Four RSCs 504–510 occupy adjacent, non-overlapping positions in a central portion of the exemplary reference image 500, forming a larger square, while the fifth RSC 502 occupies the central position within that square. The central RSC 502 may be designated as a primary RSC, and the other RSCs 504–510 may preferably designated as secondary RSCs. Of course any of the RSCs other than RSC 502 may be designated as primary, the other RSCs including RSC 502 being correspondingly designated as secondary.

Taken together, the RSCs preferably cover a substantial portion of the entire reference image, ensuring very low error probabilities during a later verification stage described below in connection with FIGS. 4A and 4B. However, each individual RSC is sufficiently small in size to enable the control unit 12 to tolerate nonlinear image distortions which may occur during the reference image acquisition step 102 if different parts of the finger are pressed against the image scanner 14 with uneven force or if the finger is applied to the image scanner 14 in a skewed position.

Returning now to FIG. 2, at step 110, the control unit 12 performs a "Reference Segment and Threshold Select" (hereinafter "RS/TS") subroutine for each RSC 502–510, starting with RSC 502. Subroutines are known in the computer programming art as functions designed to perform specific tasks requested by a main control program. One of the advantages of using subroutines is that two or more programs can use the same subroutine to perform a particular function. Modern programming techniques also encompass programmable "objects" which function similarly to subroutines. The main advantage of programmable "objects" is that once an "object" is developed to perform a particular function, it may be used in any program wishing to use that function.

Figure 3:
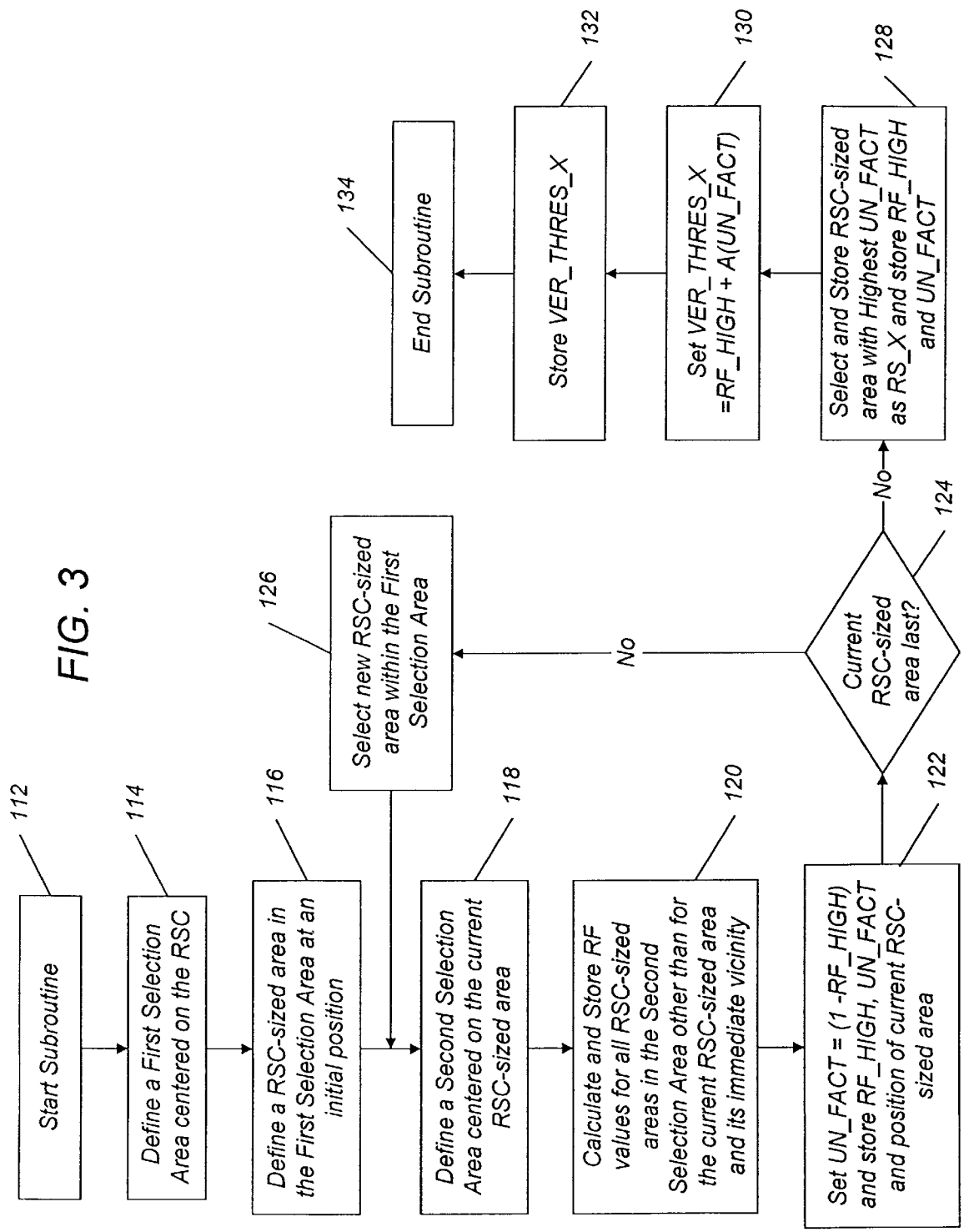

Referring now to FIG. 3, the RS/TS subroutine is executed by the control unit 12 for each RSC 502–510, starting with RSC 502, to determine optimal positions for RSCs 502–510 that cover the most unique portions of the reference image. The portions of the reference image covered by the respective RSCs 502–510 at the completion of the subroutine execution are referred to as reference segments 1 through 5 (hereinafter "RS_1" through "RS_5"). The RS/TS subroutine may also determine a set of verification threshold values (hereinafter "VER_THRES"), each VER_THRES corresponding to a particular RS of RS_1 to RS_5. The VER_THRES values are later utilized to determine a total threshold value used during the later verification stage described below in connection with FIGS. 4A–4B.

Before describing the RS/TS subroutine in greater detail, it is first noted that for greater clarity a current RS being obtained by the subroutine is expressed as RS_X, and the corresponding current VER_THRES is also expressed as VER_THRES_X, with X ranging from 1 to 5, each value of X corresponding to a particular RSC.

The RS/TS subroutine begins at step 112 and proceeds to step 114 where the control unit 12 defines a first selection area centered on the currently processed RSC (for example, RSC 502). One of the main objectives of the RS/TS subroutine that is implemented in steps 116 to 124, is to locate a most unique portion of the reference image in the first selection area that is of the same size as the RSC around which the first selection area is defined. The size of the first selection area is a matter of design choice as long as the first selection area is larger than the current RSC.

At step 116, the control unit 12 defines an RSC-sized area at an initial position in the first selection area as a possible candidate for RS_X. The initial position of the RSC-sized area is a matter of design choice. For example, the initial position of the RSC-sized area may be at the location of the current RSC or at an upper left portion of the first selection area. At step 118, the control unit 12 defines a second selection area centered on the currently defined RSC-sized area. The size of the second selection area is a matter of design choice as long as the second selection area is larger than the RSC-sized area. Referring now to exemplary FIG. 7, the RSC 502 is shown by way of example with a first selection area 512 centered thereon, a RSC sized area 514, and a second selection area 516 centered thereon.

Returning now to FIG. 3, at step 120, a set of RF values is calculated for all RSC-sized areas in the second selection area by sequentially comparing the currently defined RSC-sized area with all other RSC-sized areas in the second selection area other than RSC-sized areas in its immediate vicinity. The set of RF values is then stored in memory 16. At step 122, a uniqueness factor (hereinafter "UN_FACT") is determined for the current RSC-sized area by subtracting the highest RF value (hereinafter ("RF_HIGH")of the set of RF values determined and stored at step 120, from "1". The UN_FACT, RF_HIGH, and the position of the current RSC-sized area are then associated and temporarily stored in memory 16. At test 124, the control unit 12 determines whether the current RSC-sized area is the last RSC-sized examined area in the first selection area. If the current RSC-sized area is not the last examined RSC-sized area, the control unit 12 proceeds to step 124 where a new RSC-sized area is selected within the first selection area, and then returns to step 118 to determine the uniqueness of the newly selected RSC-sized area. Otherwise, the control unit 12 proceeds to step 128. At step 128, the control unit 12 selects an RSC-sized area having the highest UN_FACTOR from temporary storage in the memory 16, stores, in the memory 16, the portion of the reference image enclosed by the selected RSC-sized area as RS_X, and also stores UN_FACT and RF_HIGH.

At step 130, the VER_THRES_X is calculated in accordance with the following expression:

$$VER\_THRES\_X = RF\_HIGH + A(UN\_FACT)$$

where "A" is a predefined constant having a value ranging from slightly above 0 to 1 and selected as a matter of design choice. As is evident from the above expression, a higher A value increases the magnitude of the VER_THRES_X. At step 132, the VER_THRES_X is stored in the memory 16. The control unit 12 ends the RS/TS subroutine at step 134. After the RS/TS subroutine is executed by the control unit 12 for each RSC, the control unit 12 returns to step 136 in the enrollment control program of FIG. 2 with RS_1 to RS_5 and VER_THRES_1 to VER_THRES_5 values. It is noted that the positions of RS_1 to RS_5 may be quite different from the initial positions of RSCs 502 to 510 shown in FIG. 6 since the purpose of the RS/TS subroutine is to locate the most unique portions of the reference image. Referring now to FIG. 8, exemplary positions of RS_1 518 to RS_5 524 are shown on the exemplary reference image 500.

Returning now to FIG. 2, at step 136, the VER_THRES_1 to VER_THRES_5 are mathematically combined to form a total threshold (hereinafter "TOT_THRES") having the same range of values as the VER_THRESs. Preferably, TOT_THRES is a mean of the VER_THRES_1 to VER_THRES_5 values. However, TOT_THRES may be obtained by other mathematical operations such as obtaining a weighted average or a mean of the VER_THRES_1 to VER_THRES_5 values.

The TOT_THRES value is used during the later verification stage as a determining factor in admitting or rejecting a user as described below in connection with FIG. 4B. The TOT_THRES is a dynamically determined value and will vary for each fingerprint image. For example, a fingerprint image with a small number of unique portions will have a relatively low TOT_THRES, while a fingerprint image with a high number of unique portions will have a relatively high TOT_THRES. Thus, in accordance with the present invention, the TOT_THRES value is adapted to the level of uniqueness of each user's fingerprint. Alternatively, instead of computing the VER_THRES_1 to VER_THRES_5 values and determining the TOT_THRES value therefrom, the TOT_THRES value may be empirically selected as a matter of design choice. For example, the TOT_THRES value may be set at a single value ranging from 0.6 to approximately "1". It will be understood by one skilled in the art that a higher TOT_THRES provides an increased level of security by raising the similarity requirements between the reference and verify images.

At step 138, the RS_1 to RS_5 obtained at step 110 are stored in a reference file (hereinafter "REF_FILE") that is stored in the memory 16. An individual REF_FILE is preferably created by the control unit 12 for each enrolled user of the identity verification system 10 for storing reference and other data obtained from the user during the enrollment stage. A set of pixel coordinates of the RS_2 to RS_5 relative to the RS_1 is also stored in REF_FILE for use during the verification stage.

At step 140, the control unit 12 acquires additional identification data (hereinafter "ID_DATA") from the user being enrolled. The ID_DATA may be entered by the user or otherwise acquired by the input device 18, and preferably includes, but is not limited to, a personal identification code selected by the user or by the operator, the user's personal information, and an image of user. Alternatively, at least a portion of ID_DATA may be generated by the control unit 12. For example, the control unit 12 may randomly generate a personal identification code for, and assign the code to, the user being enrolled. At step 142, the ID_DATA is associated with, and stored in the REF_FILE, such that for example when a user later enters his or her personal identification code via the input device 18, a REF_FILE associated with that personal identification code (if any) may be retrieved from the memory 16 by the control unit 12. Optionally, at least a portion of the ID_DATA may be embedded in a magnetic strip card (not shown) given to the user. The control unit 12 then ends the enrollment control program at step 144.

Figure 4A:
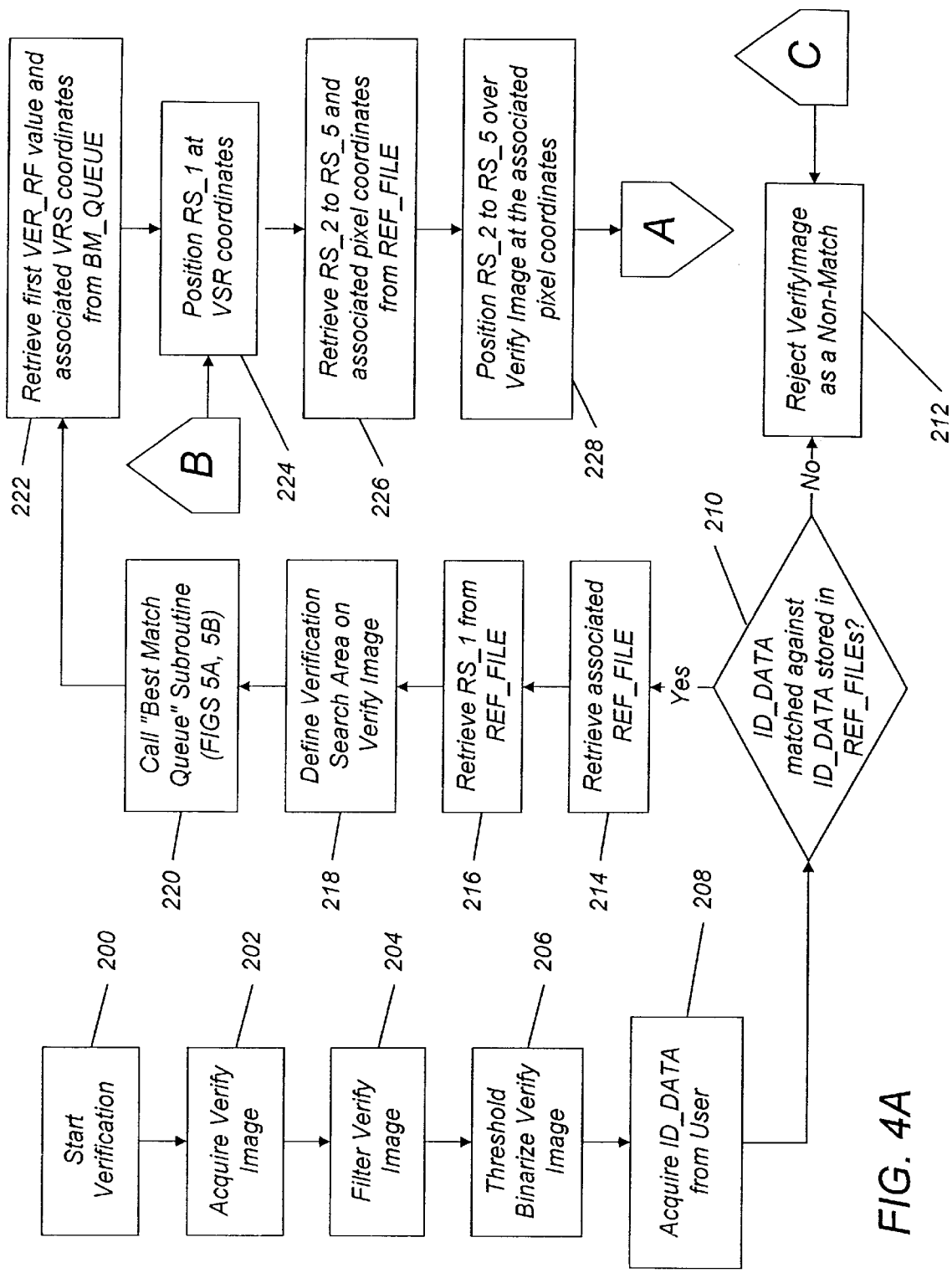
Figure 4B:
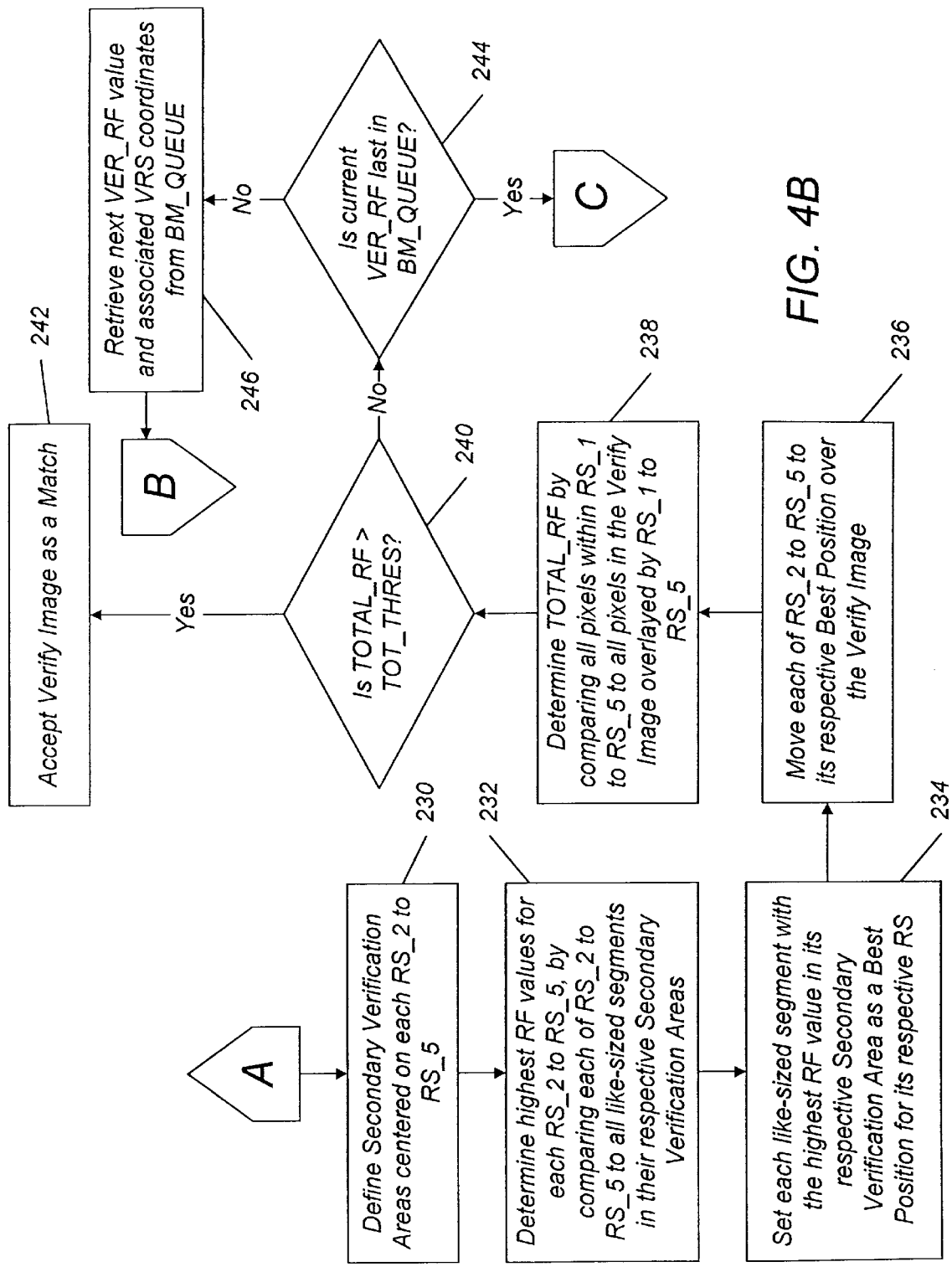

Referring now to FIG. 4A, a logic flow diagram representing a verification control program for the control unit 12 of FIG. 1 in accordance with a preferred embodiment of the present invention is shown. The verification control program is executed by the control unit 12 during the verification stage when a user seeks access to an object or area secured by the identity verification system 10. The control unit begins the program at step 200, when, for example, the user seeking access places a finger on the image scanner 14. At step 202, the control unit 12 acquires a fingerprint verify image (hereinafter "verify image") from the image scanner 14. Typically, the verify image is obtained in halftone form commonly having 256 gray levels.

At an optional step 204, the verify image may be filtered by the control unit 12 in accordance with image filtering techniques described above in connection with step 104 (FIG. 2). At an optional step 206, the verify image may be threshold binarized by the control unit 12 in accordance with the techniques described above in connection with step 106 (FIG. 2). While it is not necessary to binarize the verify image, it is preferable that the verify image is binarized to increase execution speed of the verification control program.

At step 208, ID_DATA such as the personal identification code is acquired from the user via input device 18. For example, the user may enter their personal identification code via a keyboard, or, if the personal identification code was embedded in a magnetic strip card, swipe the card through a card reader. At test 210, the acquired ID_DATA is matched against other ID_DATA stored in various REF_FILEs in the memory 16. If no match is found, the control unit 12 proceeds to step 212 where the verify image is rejected as a non-match and the verification control program is terminated, denying the user access to the secure object or area. If a match is found at test 210, the control unit 12 proceeds to step 214 where it retrieves a REF_FILE associated with the ID_DATA acquired at step 208. At step 216, the control unit 12 retrieves the RS_1 image from the REF_FILE. At step 218, the control unit 12 defines a verification search area over a substantial portion of the verify image. At step 220, the control unit 12 calls a "Best Match Queue" (hereinafter "BMQ" subroutine) to determine at least one possible best match position on the verify image corresponding to RS_1. For example, a verify image with several similar areas may have more than one apparent best match position, only one of which is correct. The purpose of the BMQ subroutine is to determine one or more of these potential best match positions in order to enable the control unit 12 to later ascertain which of them, if any, is the correct position.

Figure 5A:
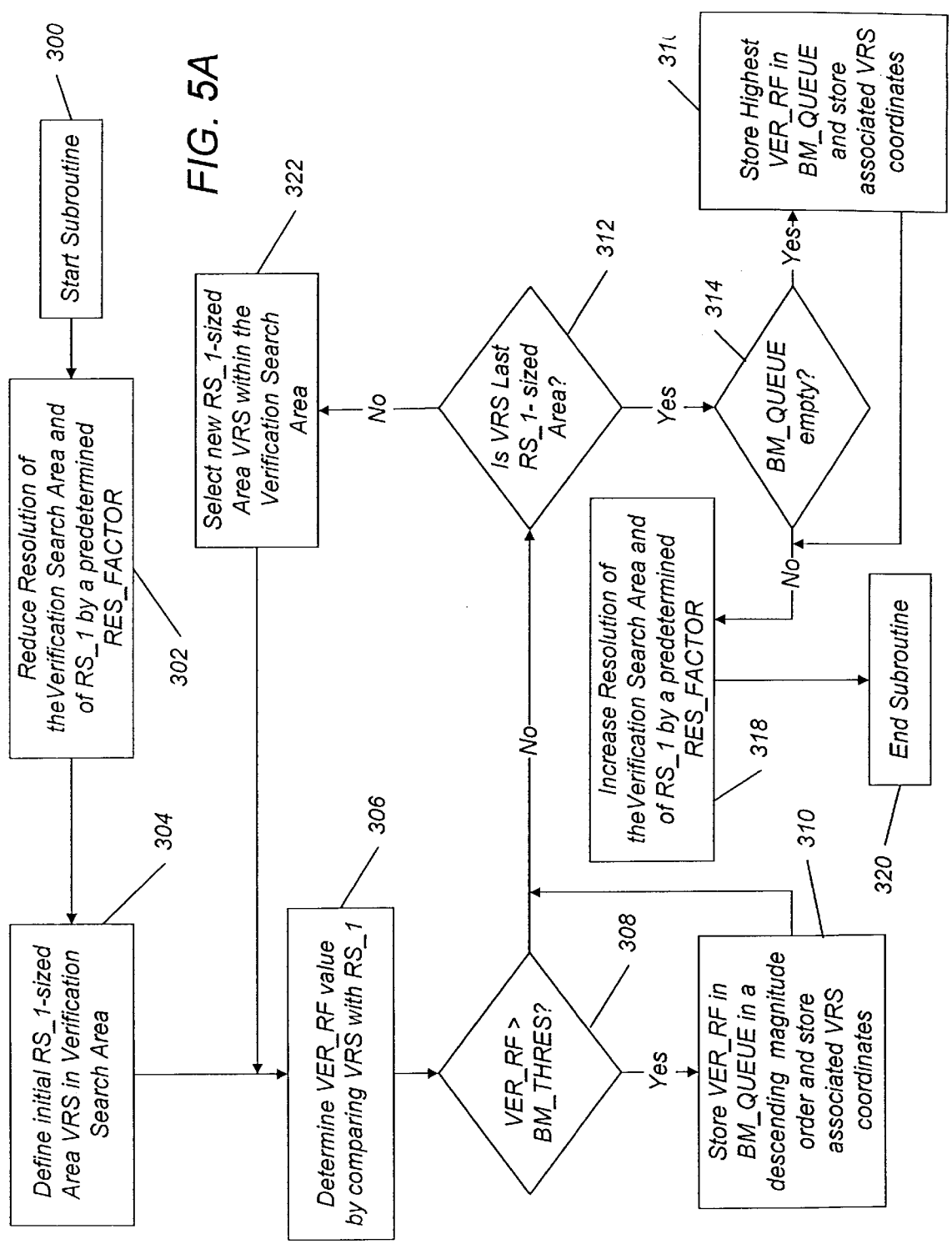
Figure 5B:
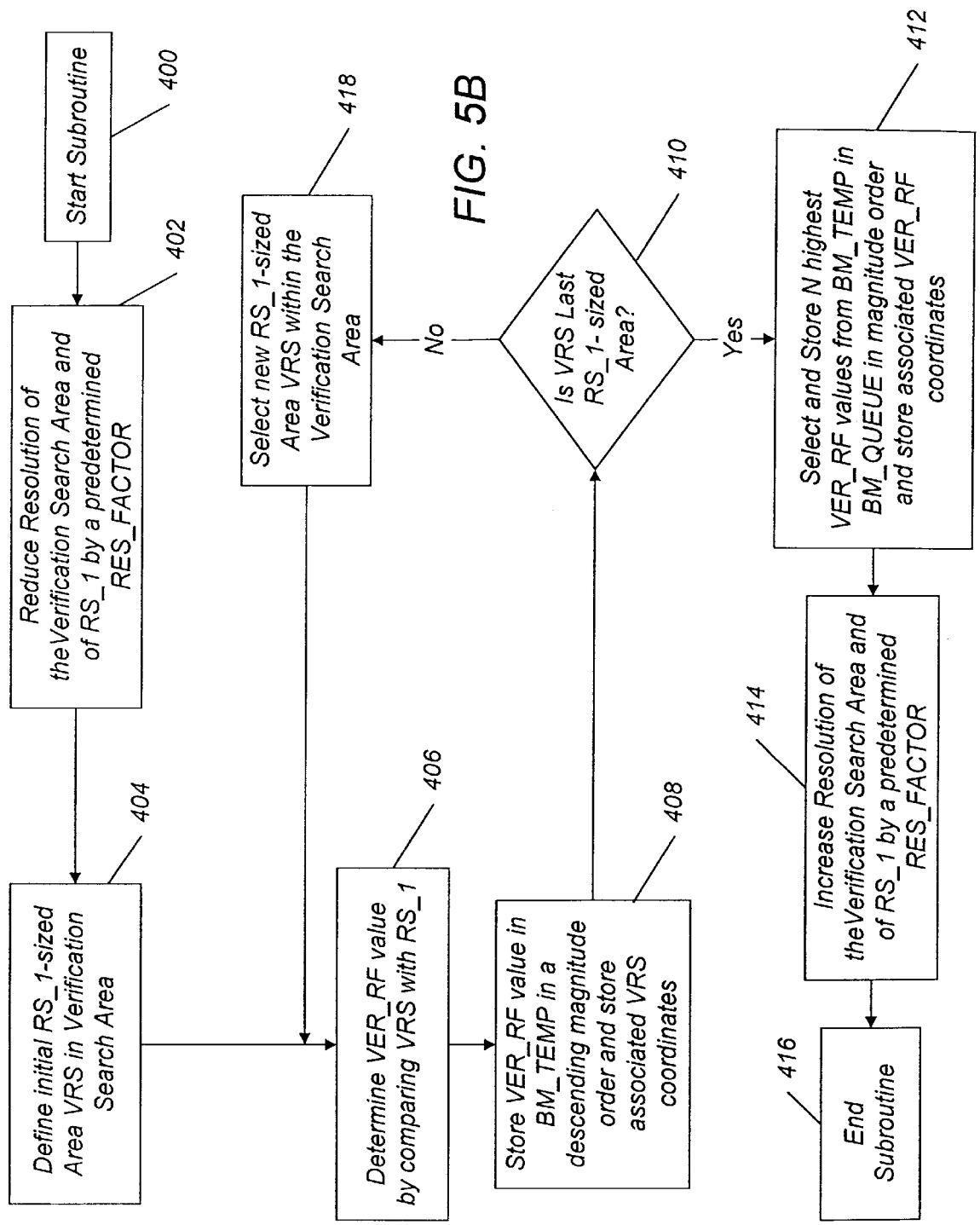

In accordance with the present invention, a first embodiment of the BMQ subroutine is shown in FIG. 5A, and a second embodiment of the BMQ subroutine is shown in FIG. 5B.

Referring to FIG. 5A, the first embodiment of the BMQ subroutine is shown. The control unit 12 begins the BMQ subroutine at step 300 and proceeds to an optional step 302 where it reduces the resolution of the verification image covered by the verification area and the resolution of RS_1 by a predetermined resolution factor (hereinafter "RES_

FACTOR") selected as a matter of design choice as an even number preferably ranging from 4 to 8. Finding one or more best-match positions of the RS_1 in the verification search area is a relatively time and computation consuming task. Temporary reduction of the resolution of both the verification search area portion of the verify image and the RS_1 itself by the RES_FACTOR results in a decrease of the image sizes and thus an increase in processing speed proportional to the magnitude of the RES_FACTOR, because best match positions become easier to locate in a reduced size image. The image resolution is preferably reduced by simply combining a number of adjacent pixels of the original image equal to the RES_FACTOR into a single pixel in the reduced resolution image. Referring to FIG. 9, an example of resolution reduction is shown where the RES_FACTOR is 4. The pixels a1–a4 in an original image 528 are combined to form a single pixel b1 in a reduced resolution image 530, and so on. If the magnitude of the RES_FACTOR was 8, all pixels a1 to a16 would be combined to form the single pixel b1. At the conclusion of the BMQ subroutine, the verification search area and RS_1 are restored to their original resolution at step 318. Steps 302 and 318 are not essential to the BMQ subroutine but provide an significant decrease in the BMQ subroutine execution time and required processing power.

Returning now to FIG. 5A, at step 304, the control unit 12 defines an initial RS_1-sized area as a first verification reference segment (hereinafter "VRS") with associated coordinates in the verification search area. Preferably, the VRS is initially positioned at a corner portion of the verification search area, such as at an upper left portion. At step 306, the control unit determines a particular verification RF (hereinafter "VER_RF") value corresponding to the currently defined VRS by comparing RS_1 to the currently defined VRS. At test 308, the control unit 12 compares the VER_RF to a best match threshold (hereinafter "BM_THRES"). The BM_THRES is a matter of design choice but is preferably selected approximately between 0.5 and 0.99. If the VER_RF exceeds the BM_THRES, the control unit 12 proceeds to step 310 where it stores the VER_RF in a best match queue (hereinafter "BM_QUEUE") in the memory 16 in a descending magnitude order and where the control unit 12 also stores associated coordinates of the currently defined VRS corresponding to the VER_RF value determined at step 306. Thus, if more VER_RF values are stored in BM_QUEUE during subsequent executions of this step, all VER_RF values are stored in the descending order of magnitude. The control unit 12 then proceeds to test 312.

If, at test 308, it is determined that the VER_RF is not greater than the BM_THRES, the control unit 12 proceeds to test 312 to determine whether the currently defined VRS is the last unique RS_1-sized area in the verification search area. If the currently defined VRS is the last unique RS_1-sized area in the verification search area, the control unit 12 proceeds to test 314, otherwise the control unit 12 proceeds to step 322. At test 314, the control unit 12 determines whether the BM_QUEUE is empty. This may occur if none of the VER_RF values exceeded the BM_THRES after multiple executions of test 308. If the BM_QUEUE is not empty, the control unit 12 proceeds to step 318. If, on the other hand, the BM_QUEUE is empty, at step 316, the control unit 12 stores the highest VER_RF and associated VRS coordinates in the BM_QUEUE and then proceeds to step 318.

At step 318, the control unit restores the resolutions of the verification search area portion of the verify image and of the RS_1 by the RES_FACTOR, and ends the BMQ subroutine at step 320. At step 322, the control unit 12 selects a new RS_1-sized area as the VRS and returns to step 306. The new VRS may be selected at step 322 by selecting an RS_1-sized area one pixel away from the previously defined VRS area.

Thus, after all RS_1-sized areas in the verification image area are examined, coordinates of at least one possible best match location and a corresponding VER_RF value are stored in the BM_QUEUE.

Referring to exemplary FIG. 10, an exemplary verification search area 532 is shown. VRS 534 is an initially defined VRS, VRS 536 is a later-defined VRS, and VRS 538 is a last VRS in the exemplary verification search area 532.

Referring now to FIG. 5B, the second embodiment of the BMQ subroutine is shown. The control unit 12 begins the BMQ subroutine at step 400 and proceeds to an optional step 402 where it reduces the resolution of the verification image covered by the verification area and the resolution of RS_1 by the RES_FACTOR such as described above in connection with step 302 (FIG. 5A). At step 404, the control unit 12 defines an initial RS_1-sized area as a first verification reference segment (hereinafter "VRS") with associated coordinates in the verification search area. Preferably, the VRS is initially positioned at a corner portion of the verification search area, such as at an upper left portion. At step 406, the control unit determines a VER_RF value corresponding to the currently defined VRS by comparing RS_1 to the currently defined VRS.

At step 408, the control unit 12 stores the VER_RF value in a best match temporary buffer (hereinafter "BM_TEMP") in the memory 16 in a descending magnitude order and also stores associated coordinates of the currently defined VRS corresponding to the VER_RF value determined at step 406. Thus, as more VER_RF values are stored in BM_TEMP during subsequent executions of this step, all VER_RF values are stored in the descending order of magnitude. At test 410, the control unit determines whether the currently defined VRS is the last unique RS_1-sized area in the verification search area. If the currently defined VRS is the last unique RS_1-sized area in the verification search area, the control unit 12 proceeds to step 412, otherwise the control unit 12 proceeds to step 418.

At step 412, the control unit 12 selects N highest VER_RF values and associated VRS coordinates from BM_TEMP and stores them in the BM_QUEUE, where N is an integer number selected as a matter of design choice. At step 414 the control unit restores the resolutions of the verification search area portion of the verify image and of the RS_1 by the RES_FACTOR, and ends the BMQ subroutine at step 416. At step 418, the control unit 12 selects a new RS_1-sized area as the VRS and returns to step 406. The new VRS may be selected at step 418 by selecting an RS_1-sized area one pixel away from the previously defined VRS area.

Thus, after all RS_1-sized areas in the verification image area are examined, coordinates of N possible best match locations and their corresponding VER_RF values are stored in the BM_QUEUE.

After executing the BMQ subroutine described in FIG. 5A or the one described in FIG. 5B, the control unit 12 returns to FIG. 4A to step 222 where it retrieves the first (i.e., the highest) VER_RF value and associated VRS coordinates from the BM_QUEUE. At step 224, the control unit 12 positions the RS_1 over the verify image at the currently retrieved VRS coordinates. At step 226, the control unit 12 retrieves RS_2 to RS_5 from the REF_FILE, and at step 228 positions RS_2 to RS_5 over the verify image at their respective pixel coordinates previously stored at step 136 (FIG. 2) relative to the current position of the RS__1.

At step 230, the control unit 12 defines secondary verification areas centered on each of RS__2 to RS__5. The secondary verification areas are preferably larger than the respective RS__2 to RS__5. At steps 232 to 236, the control unit 12 locates the most likely (i.e. "best") position for each RS in its respective secondary search area and moves each RS to its respective best position. At step 232, the control unit 12 determines a set of RF values for each of RS__2 to RS__5 by comparing each individual RS to all like-sized image segments in their respective secondary verification area. For each RS__2 to RS__5 a position of a like-sized segment having a highest RF value in its respective secondary verification area is then identified. At step 234, the control unit 12 sets each of the like sized segment positions determined at step 232 as a best position for its respective RS. At step 236, the control unit 12 moves each of the RS__2 to RS__5 to its respective best position over the verify image.

At step 238, the control unit 12 determines a total RF (hereinafter "TOTAL__RF") by comparing all pixels within the RS__1 to RS__5 to all pixels in the verify image portion overlaid by the current positions of the RS__1 to RS__5. This approach thus compares a large portion of the original reference image represented by RS__1 to RS__5 to a large portion of the verify image overlaid by a multi-segment global template consisting of the area defined by the dynamically determined best match positions of the RS__1 to RS__5 to determine a summary RF representative of the similarity between the reference image and the verify image. Because large image portions are compared and a global RF is obtained therefrom in contrast to previously known systems, variations between the reference image and the verify image such as those caused by a cut or dirt on a finger, improper finger placement or finger skewing on the image scanner 14, or dirt on the image scanner 14 itself, will have little or no effect on the accuracy of the comparing process.

At test 240, the control unit 12 compares the TOTAL__RF to the TOT__THRES determined at step 134 (FIG. 2) or otherwise selected. If the TOTAL__RF is greater than the TOT__THRES, the control unit 12 proceeds to step 242 where the verify image is accepted as substantially similar to the reference image and the user is granted access to the secure object or area. Otherwise the control unit 12 proceeds to test 244 where it determines whether the currently selected VER__RF is the last one in the BM__QUEUE. If the current VER__RF is not the last one, the control unit 12 proceeds to step 246 where it retrieves the nest highest VER__RF value and its associated VRS coordinates from the BM__QUEUE and then returns to step 224. Otherwise the control unit 12 proceeds to step 212.

It is noted that the identity verification system 10 of the present invention may be implemented in a variety of other fingerprint matching applications with minor modifications. For example, instead of obtaining a user's ID__DATA and later retrieving an associated REF__FILE, the identity verification system 10 can simply obtain a verify image from a user seeking access during the verification stage and then sequentially compare the obtained verify image to all reference images stored in the REF__FILEs in the memory 16 until either a match is found or the user is rejected when the last reference image is not matched to the obtained verify image successfully. This modification can also be used in a law enforcement application where a suspect's verify fingerprint image is automatically sequentially matched against all reference fingerprint images stored in a law enforcement database.

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A method for comparing a first image of a predefined image resolution comprising a first plurality of pixels and a second image of the predefined image resolution comprising a second plurality of pixels to determine if the images are substantially similar, said method being implemented in a data processing system having a memory, comprising the steps of:

(a) acquiring the first image;

(b) defining a plurality of adjacent reference templates positioned over a substantial portion of the first image, wherein each of said reference templates encloses a different portion of the first image;

(c) designating one reference template of said plurality of reference templates as a primary reference template, and all other reference templates as secondary reference templates;

(d) defining around each of said reference templates, a corresponding individual first selection area centered on each reference template, each of said first selection areas being larger than its respective reference template;

(e) determining a best position for each reference template within said corresponding first selection area, wherein said best position of each reference template is representative of a most unique portion of the first image within the respective first selection (g) storing, in the memory as a reference file, the most unique portion of each respective first selection area, wherein the most unique portion corresponding to said primary reference template is designated as a primary reference segment and wherein each most unique portion corresponding to a particular one of said plurality of said secondary reference templates is designated as a plurality of said secondary reference segments;

(h) storing a set of coordinate positions of each of secondary reference segments relative to said primary reference segment in said reference file in the memory;

(i) defining a reference area comprising the pixels of the first image within said primary reference segment and said plurality of secondary reference segments;

(j) acquiring the second image;

(k) defining a first search area over a substantial portion of the second image;

(l) retrieving, from said reference file in the memory, said primary reference segment and said plurality of secondary reference segments;

(m) comparing said primary reference segment with all primary reference segment-sized portions of the second image within said first search area to determine a location of a closest match between said primary reference segment and a like-sized portion of the second image, wherein said like-sized portion is designated as a closest match portion;

(n) positioning the primary reference segment at said at least one closest match location and said plurality of secondary reference segments over said second image in accordance with said set of coordinate positions of each said secondary reference segment relative to said primary reference segment;

(o) defining a plurality of second search area templates, each second search area template corresponding to each of said secondary reference segments, each second search area template being centered on of each said corresponding secondary reference segments;

(p) comparing each secondary reference segment with all secondary reference segment-sized portions of the second image within its corresponding second search area to determine a best match position for each secondary reference segment within its corresponding second search area to obtain a plurality of best match portions of the second image corresponding to said plurality of secondary reference segments;

(q) defining a verification area comprising pixels of the second image within said closest match portion and said plurality of best-match portions; and (r) comparing said reference area to said verification area to determine a total response value, said total response value being indicative of the degree of similarity between said reference area and said verification area.

2. The method of claim 1, further comprising the step of:

(s) after said step (r) comparing said total response value to a predetermined total threshold, and when said total response value exceeds said predetermined total threshold, accepting the second image as substantially similar to the first image, and otherwise rejecting the second image as being not substantially similar to the first image.

3. The method of claim 2, wherein said step (m) comprises the steps of:

(gg) comparing said primary reference segment with each primary reference segment-sized area having a set of associated coordinates in said first search area to determine a predetermined amount of highest verification response values and said associated coordinates of corresponding particular reference segment-sized areas, each verification response value being representative of, and having a magnitude proportional to, the degree of similarity between said primary reference segment and a corresponding particular primary reference segment-sized area;

(hh) storing, in a best match queue in the memory, said predetermined amount of highest verification response values in a descending order of magnitude and storing said sets of associated coordinates of said particular primary reference segment-sized areas that each correspond to a particular verification response value of said predetermined amount of highest verification response values;

wherein said step (n) comprises the steps of:

(ii) retrieving from said best match queue a set of associated coordinates of a first primary reference segment-sized area corresponding to a highest verification response value of said predetermined amount of highest verification response values;

(jj) positioning said primary reference segment at said retrieved set of associated coordinates over said second image;

(kk) positioning said plurality of secondary reference segments over said second image in accordance with said set of coordinate positions of each said secondary reference segment; and wherein said step (s) comprises the step of:

(ll) comparing said total response value to a predetermined total threshold, and when said total response value exceeds said predetermined total threshold, accepting the second image as substantially similar to the first image, and otherwise when at least one unretrieved set of associated coordinates of a primary reference segment-sized area remains in said best match queue, retrieving from said best match queue a set of associated coordinates of a first primary reference segment-sized area corresponding to a next highest verification response value of said predetermined amount of highest verification response values and returning to said step (jj), and otherwise rejecting the second image as being not substantially similar to the first image and terminating the comparing process.

4. The method of claim 2, wherein said step (m) comprises the steps of:

(mm) comparing said primary reference segment with each primary reference segment-sized area having a set of associated coordinates in said first search area to determine a plurality of verification response values and said associated coordinates of corresponding particular reference segment-sized areas, each verification response value being representative of, and having a magnitude proportional to, the degree of similarity between said primary reference segment and a corresponding particular primary reference segment-sized area;

(nn) comparing each verification response value of said plurality of verification response values to a predetermined verification response threshold, and storing, in a best match queue in the memory, all verification response values that have exceeded said predetermined verification response threshold in a descending order of magnitude and storing said sets of associated coordinates of said particular primary reference segment-sized areas that each correspond to a particular verification response exceeding said predetermined verification response threshold, wherein when none of said plurality of verification response values exceed said predetermined verification response threshold, storing, in said best match queue in the memory, a highest verification response value and a set of associated coordinates of a particular primary reference segment-sized areas corresponding to said highest verification response value;

wherein said step (n) comprises the steps of:

(oo) retrieving from said best match queue a set of associated coordinates of a first primary reference segment-sized area corresponding to a highest verification response value stored in said best match queue;

(pp) positioning said primary reference segment at said retrieved set of associated coordinates over said second image;

(qq) positioning said plurality of secondary reference segments over said second image in accordance with said set of coordinate positions of each said secondary reference segment; and wherein said step (s) comprises the step of:

(rr) comparing said total response value to a predetermined total threshold, and when said total response value exceeds said predetermined total threshold accepting the second image as substantially similar to the first image, and otherwise when at least one unretrieved set of associated coordinates of a primary reference segment-sized area remains in said best match queue, retrieving from said best match queue a set of associated coordinates of a first primary reference segment-sized area corresponding to a next highest verification response value stored in said best match queue, and returning to said step (pp), and otherwise rejecting the second image as being not substantially similar to the first image and terminating the comparing process.

5. The method of claim 1, further comprising the step of:
(t) after said step (a) but before said step (b), filtering the first image to remove at least signal noise and brightness variations therefrom.

6. The method of claim 1, further comprising the step of:
(u) after said step (a) but before said step (b), binarizing the second image in accordance with a predefined binarization threshold.

7. The method of claim 1, further comprising the step of:
(v) after said step (j) but before said step (k), filtering the second image to remove at least signal noise and brightness variations therefrom.

8. The method of claim 7, further comprising the step of:
(w) after said step (v) but before said step (k), binarizing the second image in accordance with a predefined binarization threshold.

9. The method of claim 1, wherein said step (e) further comprises the steps of:
(x) for each of said reference templates:
  (1) for each reference template-sized area in said corresponding first search area:
    (A) defining a corresponding second selection area centered on a reference template-sized area, said second selection area being larger than said reference template-sized area;
    (B) comparing a set of pixels of said first plurality of pixels that are enclosed by said reference template-size area to other sets of pixels of said first plurality of pixels that are enclosed by each of a plurality of other reference template-sized areas within said second search area to determine a plurality of response function values for said reference template-sized area, each response function value of said plurality of response function values being representative of, and proportional to, a degree of similarity between said reference template-sized area and a different one of said plurality of other reference template-sized areas, wherein a lower response function value is representative of a low degree of similarity, and a higher response function value is representative of a high degree of similarity, and wherein a maximum value of a response function is unity;
    (C) determining a uniqueness factor of said reference template-sized area in accordance with a following expression:

uniqueness factor=(1−RF_HIGH)

wherein RF_HIGH is a highest response function value of said plurality of response function values; and
  (2) storing the position of a reference template-sized area having a highest uniqueness factor as a best-match position for said reference template.

10. The method of claim 9, wherein said step (x) further comprises the steps of:
(3) determining a reference threshold value in accordance with a following expression:

reference threshold value=RF_HIGH+A(uniqueness factor), wherein A is a predefined threshold constant.

11. The method of claim 10, further comprising the steps of:
(y) after said step (e) and before said step (f), determining a total threshold value by one of: determining a weighted average of said reference threshold values obtained at said step (x)(3), and determining a mean of said reference threshold values obtained at said step (x)(3); and
(z) after said step (h) and before said step (j), storing said total threshold value in said reference file in the memory.

12. The method of claim 1, further comprising the steps of:
(aa) after said step (a) and before said step (j) acquiring from a user additional identifying data comprising said user's personal identification code; and
(bb) storing said additional identifying data in, and associating said additional identifying data with said reference file in the memory.

13. The method of claim 12, wherein said step (aa) comprises the step of randomly selecting additional identifying data comprising said user's personal identification code.

14. The method of claim 12, further comprising the steps of:
(cc) after said step (k) and before said step (l), acquiring a personal identification code from a user seeking verification of the second image being substantially similar to the first image; and
(dd) determining whether a match exists between said acquired personal identification code and said personal identification code stored in said reference file in the memory, and when a match exists proceeding to said step (l), and otherwise rejecting the second image as being not substantially similar to the first image and terminating the comparing process.

15. The method of claim 12, wherein said additional identifying data further comprises at least one of: said user's personal information and an image of said user.

16. The method of claim 1, wherein said primary reference segment is of a predefined segment resolution, further comprising the steps of:
(ee) after said step (l) and before said step (m), reducing the image resolution of the second image and said segment resolution of said primary reference segment by a predefined resolution factor; and
(ff) after said step (m) and before said step (n) increasing the image resolution of the second image and said segment resolution of said primary reference segment by said predefined resolution factor.

17. A data processing system for comparing a first image comprising a first plurality of pixels and a second image comprising a second plurality of pixels to determine if the images are substantially similar, said system comprising:
scanning means for acquiring the first and the second images;
memory means for storing data; and control means, connected to said scanning means and said memory means, operable for:

causing said scanning means to acquire the first image;

defining a plurality of adjacent reference templates positioned over a substantial portion of the first image, wherein each of said reference templates encloses a different portion of the first image;

designating one reference template of said plurality of reference templates as a primary reference template, and all other reference templates as secondary reference templates;

defining around each of said reference templates, a corresponding individual first selection area centered on each reference template, each of said first selection areas being larger than its respective reference template;

determining a best position for each reference template within said corresponding first selection area, wherein said best position of each reference template is representative of a most unique portion of the first image within the respective first selection area, said most unique portions being of the same size as the respective reference templates;

moving each reference template to its corresponding best position;

storing, in said memory means as a reference file, the most unique portion of each respective first selection area, wherein the most unique portion corresponding to said primary reference template is designated as a primary reference segment and wherein each most unique portion corresponding to a particular one of said plurality of said secondary reference templates is designated as a plurality of said secondary reference segments;

storing, in reference file in said memory means, a set of coordinate positions of each of secondary reference segments relative to said primary reference segment;

defining a reference area comprising the pixels of the first image within said primary reference segment and said plurality of secondary reference segments;

causing said scanning means to acquire the second image;

defining a first search area over a substantial portion of the second image;

retrieving, from said reference file in said memory means, said primary reference segment and said plurality of secondary reference segments;

comparing said primary reference segment with all primary reference segment-sized portions of the second image within said first search area to determine a location of a closest match between said primary reference segment and a like-sized portion of the second image, wherein said like-sized portion is designated as a closest match portion;

positioning the primary reference segment at said at least one closest match location and said plurality of secondary reference segments over said second image in accordance with said set of coordinate positions of each said secondary reference segment relative to said primary reference segment;

defining a plurality of second search area templates, each second search area template corresponding to each of said secondary reference segments, each second search area template being centered on of each said corresponding secondary reference segments;

comparing each secondary reference segment with all secondary reference segment-sized portions of the second image within its corresponding second search area to determine a best match position for each secondary reference segment within its corresponding second search area to obtain a plurality of best match portions of the second image corresponding to said plurality of secondary reference segments;

defining a verification area comprising pixels of the second image within said closest match portion and said plurality of best-match portions;

comparing said reference area to said verification area to determine a total response value, said total response value being indicative of the degree of similarity between said reference area and said verification area; and comparing said total response value to a predetermined total threshold, and when said total response value exceeds said predetermined total threshold, accepting the second image as substantially similar to the first image, and otherwise rejecting the second image as being not substantially similar to the first image.

* * * * *